United States Patent [19]
Blouin

[11] 3,991,225
[45] Nov. 9, 1976

[54] METHOD FOR APPLYING COATINGS TO SOLID PARTICLES

[75] Inventor: Glenn M. Blouin, Florence, Ala.

[73] Assignee: Tennessee Valley Authority, Muscle Shoals, Ala.

[22] Filed: Dec. 12, 1974

[21] Appl. No.: 532,034

Related U.S. Application Data

[60] Division of Ser. No. 438,875, Feb. 1, 1974, Pat. No. 3,877,415, which is a continuation-in-part of Ser. No. 382,153, July 24, 1973, now Defensive Publication No. T927,005.

[52] U.S. Cl. .................................. 427/3; 427/212; 427/214; 427/215; 427/220; 427/221; 427/242

[51] Int. Cl.² ................. A61K 9/00; B05D 7/00

[58] Field of Search .......... 427/212, 214, 215, 216, 427/217, 218, 219, 220, 221, 222, 242, 3; 118/303, 314, 315, DIG. 2

[56] References Cited
UNITED STATES PATENTS

| | | | |
|---|---|---|---|
| 2,340,567 | 2/1944 | Sargent | 427/215 |
| 3,092,489 | 6/1963 | Smith | 71/64 |
| 3,101,040 | 8/1963 | Lanz | 427/212 |
| 3,285,223 | 11/1966 | Sahlin | 427/242 |
| 3,342,577 | 9/1967 | Blouin et al. | 71/3 |
| 3,390,648 | 7/1968 | Martin | 427/3 |
| 3,398,191 | 8/1968 | Thompson et al. | 260/555 |
| 3,573,966 | 4/1971 | Hostetler | 427/3 |

*Primary Examiner*—Ronald H. Smith
*Assistant Examiner*—Dennis C. Konopacki
*Attorney, Agent, or Firm*—Robert A. Petrusek

[57] ABSTRACT

The apparatus provides a homogeneous (with respect to particle size), dense, mass of sized particles in random motion so that highly uniform coatings of the same or of different solids can be applied to each particle by conventional spray-coating with the liquified coating material(s). The apparatus is a horizontal rotary drum containing lifting flights. A novel deflector pan is fixed in space inside the upper section of the drum which deflects particles falling from the lifting flights to the side of the drum where they form a narrow, dense falling cascade. The coating material is sprayed onto the cascading particles, preferably as they free-fall after leaving the lower edge of the pan. However, if desired, some or most of the coating material may be directed onto the top edge of the moving bed including the juncture of the cascade therewith.

2 Claims, 2 Drawing Figures

METHOD FOR APPLYING COATINGS TO SOLID PARTICLES

The invention herein described may be manufactured and used by or for the Government for governmental purposes without the payment to me of any royalty therefor.

CROSS REFERENCES TO RELATED APPLICATIONS

This application is a divisional application of my copending application Ser. No. 438,875, filed Feb. 1, 1974, now U.S. Letters Pat. No. 3,877,415, issued Apr. 15, 1975, which application Ser. No. 438,875 is in turn a continuation-in-part of my copending application Ser. No. 382,153, filed July 24, 1973 (now Defensive Publication T927,005), both for AND APPARATUS FOR APPLYING COATINGS TO SOLID PARTICLES.

BACKGROUND OF THE INVENTION

1. Field of the Invention

The present invention relates to an improvement in the uniformity of one or more coatings of solid or semisolid materials applied on particulate substrates; more particularly it relates to highly uniform and effective coatings which may be either of the same, or of different composition, as the particulate substrate, as well as layers, each of a different composition, which may be applied consecutively and uniformly in the desired proportions; and still more particularly it relates to coating media that are normally solids or semisolids at ambient temperatures but that can be reduced to a sprayable liquid state by melting or by dissolution or suspension in an appropriate solvent and that can be quickly returned to the solid or semisolid state by cooling below the fusion temperature or by rapid evaporation of the solvent, it being understood, of course, that such cooling may be achieved by passing a cooling gas, such as ambient air, through the unit in contact with the product, or more simply by maintaining the particulate feed temperature at a sufficiently low temperature that the resulting product emerges at a temperature below the fusion temperature of the coating medium, and that evaporation of a solvent may be achieved by passing heated gases through the unit in contact with the product.

The invention is particularly well-suited to the application of uniform coatings of fusible compounds, elements, or mixtures on particulate, water-soluble fertilizer compounds for the purpose of producing controlled-release fertilizers, but is not limited to processing materials of this type.

The application of coatings, or encapsulations, on particulate substrate by the spraying of melts, solutions or suspensions onto moving beds of the particles in a wide variety of types of equipment is well known in the prior art. The application of coatings of the same material as the particulate substrate is commonly referred to as granulation and is widely used in the fertilizer industry, among others. Coating with materials different than the particulate substrate is more aptly termed coating, or encapsulation, and is also practiced in the fertilizer industry to some extent, but more widely in the production of pharmaceuticals such as pills or tablets and food products such as candies or nuts. Coating per se is not practiced widely in fertilizer industry at this time because of the difficulty in obtaining adequately uniform coatings at high-tonnage capacities with low-cost coating media.

The most demanding requirements for uniformity of coating, both from the standpoint of completeness of the coating around each individual particle and of maintaining the same relative proportions of the coating medium to the substrate throughout the mass of particles occur in the production of certain pharmaceuticals. In this field, the coating may be either an active ingredient which must be proportioned correctly on each substrate pill, or it may be a permeable, inert coating designed to release the medically active component slowly over a period of hours. In the latter case, nonuniform coatings with imperfections may release dangerous amounts of the substrate drug too rapidly. On the other hand, the high price and low tonnage production of drugs justifies the use of high-cost coating media in small sophisticated expensive coating units that are usually operated in relatively small batches.

It is in the fertilizer industry that the overall requirements for an economical continuous, high-capacity coating unit, capable of applying a highly uniform coating, are most difficult to meet. Although it is apparent to those versed in the art that the instant invention as disclosed in the following sections is readily adaptable on a small scale to the requirements of the pharmaceutical industry, or to other similar applications; they will also recognize that the instant invention is particularly adaptable to the requirements in the fertilizer industry for simple, low-cost equipment and for high-tonnage production capacity. Therefore, the discussions and disclosures in the following sections describe the prior art and the application of the instant invention to coated fertilizer production, both for the purpose of granulation, i.e., gradual increase of undersized nuclei to product size by successive layering, or coating, of the same or dissimilar fertilizer compounds; and for the purpose of applying permeable or semipermeable coatings of natural or synthetic polymeric compounds, oils, waxes, asphaltic mixtures, sulfur, and combinations of these materials to product size particulate fertilizer substrate in order to provide a cnrolled-release fertilizer, a product of proven desirable characteristics to those versed in the art, provided that it can be produced in simple equipment at a reasonable cost.

2. Description of the Prior Art

U.S. Pat. Nos. 3,117,020, T. Fabris et al (Jan. 7, 1964), 3,165,395, I. W. McCamy et al (Jan. 12, 1965), and 3,211,522, R. A. Shurter et al (Oct. 12, 1965) disclose the granulation of undersized fertilizer compound nuclei (recycled fines from product screened) by spraying a hot, concentrated aqueous solution or a nearly anhydrous melt of the compound onto a rolling bed of the nuclei in an inclined, rotating pan. Although there is some coating action, most of the granulation, or increase to product size, is accomplished by agglomeration, or sticking together, of a number of the nuclei by the solidifying melt or solution. The granules are relatively rough and irregular, compared with layer granulation (see later section), and coating per se is minimal. The unit has little application as a true coating unit because of its natural classification action.

In U.S. Pat. No. 2,815,376, R. E. Knowlton et al (Dec. 3, 1957), there is disclosed the granulation of fertilizer compounds by the spraying, or simple mixing, of the undersized fertilizer compound nuclei with a hot solution or melt of the compound in a paddle mixer (blunger or pugmill). Again, granulation is by agglomeration of several nuclei into a single, larger particle by the solidifying melt. Little coating action is achieved and the particles are rough and irregular.

It has also been shown that granulation, predominantly by a true coating, or layering, action can be accomplished by spraying the hot solution or melt of a fertilizer compound into a fluidized bed of undersized compound nuclei. In U.S. Pat. No. 2,600,253, W. A. Lutz (June 10, 1952) ammonium nitrate or ammonium sulfate fertilizers are produced by reacting ammonia and nitric acid or sulfuric acid in a fluidized bed of undersized ammonium nitrate or ammonium sulfate particles. In other applications, principally in Europe, a hot melt or concentrated solution of the compound is sprayed into the fluidizing gas (hot air) at the bottom of the fluidized bed. The fluidized bed does achieve the truly random motion of the substrate particles, and therefore a homogeneous mass with respect to particle size, that is so necessary in uniformly coating particles of varying sizes. However, the fluidization process is inherently costly; it requires close control, and it does not permit visual examination of the sprays or product in the coating section.

In the fertilizer industry, granulation, i.e., increase in particle size from undersize (recycled fines) to product size by coating, and coating for the purpose of imparting special characteristics to the fertilizer substrate, such as controlled release or anticaking properties, is most widely practiced in essentially horizontal rotary drums either with or without internal lifting vanes or flights. U.S. Pat. No. 3,398,191, J. B. Thompson et al (Aug. 20, 1968), discloses the granulation of urea or ammonium nitrate by spraying an essentially anhydrous melt (98-99.5 percent) of the coating compound from multiple spray heads spaced at intervals along the entire length of the coating section onto a rolling bed and into a showering curtain of undersized nuclei (recycled fines) maintained in motion by the rotation of a slightly inclined (from horizontal) rotating drum equipped with longitudinal lifting vanes, or flights, specially designed to form continuous longitudinal curtains of falling particles that move in succession across the entire cross sectional area of the contact, or coating, zone of the drum in a manner familiar to those versed in the art of horizontal rotary drum coolers and dryers. Transverse retaining rings, or dams, at the feed end and discharge end of the coating section maintain an adequate depth of bed. Cooling air (ambient temperature) is drawn countercurrently through the showering curtains of falling particles to cool and solidify the layers of melt on the nuclei. The drum is extended beyond the contact zone to a cooling zone, equipped with the lifting flights, but without spray heads, with which to further cool the product with the countercurrent flow of air.

Other essentially identical examples of this form of prior art featuring the falling curtain across the full cross sectional area of the rotary drum are disclosed in U.S. Pat. Nos. 3,092,489, Smith (June 4, 1963), 3,227,789, Tytus et al (Jan. 4, 1966), and 3,232,703, Thompson et al. (Feb. 1, 1966).

The falling curtains of particles across the full cross sectional area of the drum, as described in the above prior art, approaches the degree of random motion of substrate, and therefore of homogeneity with respect to particle size, that is so important to the uniform coating of a mass of particles of different sizes, but it is now believed that the arrangement of spary heads within the shower of falling particles, and therefore in actual contact with many of the falling particles as a result of the falling curtains across the entire cross sectional area of the drum, has certain serious disadvantages. Among the most serious of these disadvantages are (1) the lack of control of the spray distance, i.e., the distance that the individual droplets of atomized liquid spray travels before impinging upon the moving substrate particles; some of the particles fall on each spray head, some immediately in front of it, some fall at the optimum distance, and some fall well beyond the optimum distance but are still contacted by the spray. This leads to agglomeration of the substrate particles when too short or too rough, ineffective coatings when too far; (2) the actual contact of many of the falling particles with the hot spray heads leads to melted substrate, which drips onto the substrate bed, causing serious agglomeration of some of the substrate; (3) visual monitoring of the individual spray operation is impossible; and (4) dusting is serious when the entire section of the rotating drum is filled with falling particles, dust formed by attrition, and solidified spray mist, all of which can be carried from the system by the cooling or heating air flowing through the coating unit. This increases antipollution equipment requirements.

The coating procedure as practiced by Blouin et al (U.S. Pat. No. 3,295,950, Jan. 3, 1967; U.S. Pat. No. 3,342,577, Sept. 19, 1967) and by Shirley et al (patent application Ser. No. 346,711, filed Mar. 30, 1973 assigned to the assignee of the instant application and abandoned in favor of application Ser. No. 449,322, filed Mar. 8, 1974, now U.S. Letters Pat. No. 3,903,333, issued Sept. 2, 1975), are almost identical in nature, i.e., the directing of the atomized coating material only onto the rolling bed of substrate in a horizontal rotary drum having a relatively smooth interior (no lifting vanes or flights, see U.S. Pat. No. 2,741,545, Nielsson, Apr. 10, 1956). The latter art, i.e., Shirley, discloses certain improvements in the former which, according to the example data disclosed, does result in somewhat more uniform coatings than those of the former art.

However, both practice essentially the same approach as described above and, therefore, both suffer from the same serious disadvantage that precludes a truly homogeneous moving bed of particles of different sizes and therefore true uniformity of the coating, namely, the segregation by particle size of particles of varying sizes (always present in fertilizer production, for example) that occurs in a smooth, horizontal rotary drum. This segregation, or demixing, is well documented in the extensive work of Campbell et al [Chemical Engineering 73 (19), 179–185 (Sept. 12, 1966)] and McDonald et al [British Chemical Engineering 7 (10), 749–753 (Oct. 1962)--Part I; ibid 7 (11), 823–27 (Nov. 1962)--Part II; and ibid 7 (12), 922–23 (Dec. 1962)--Part III]. Although the degree of demixing, or segregation, that occurs in a smooth drum may be reduced by proper choice of operating and equipment variables such as bed depth, or degree of drum loading, drum speed (expressed as percent of critical speed, the critical speed, i.e., revolutions/minute, of a smooth drum being defined as 76.5/ D, where $D$ = drum diameter in feet), and ratio of drum diameter to drum length, it cannot be eliminated. As a result, smaller particles tend to segregate from the larger particles by going to the point of lowest particle velocity, namely, the center of the cross sectional area of the bed and pass on through the drum without coming to the surface of the bed. This, of course, prevents these particles from being coated by the liquid spray.

It is now believed that the present invention as described in succeeding sections of this application will overcome the serious disadvantages encountered in the practice of prior art previously discussed.

It is therefore the primary object of the present invention to provide essentially random motion of particles with respect to each other and therefore a truly homogeneous moving mass of particles in a simple horizontal rotary drum so that in any otherwise simple liquid spray coating process, all of the particles will be equally exposed to the liquid spray material as they pass through the drum regardless of range of size or shape of the particles, thus providing a means of producing highly uniform coatings on the particles.

It is a further object of the present invention to provide the means of applying highly uniform coatings to particulate matter by spray coating with a liquid media in a simple, widely used type of unit that has a high-tonnage production capacity per unit of cost of the equipment.

SUMMARY OF THE INVENTION

The present invention comprises, in general, an apparatus that is designed to continuously produce a moving mass of solid particulate material, each particle of which is in a state of essentially random motion with respect to the other particles, thus rendering the moving mass essentially homogeneous with respect to particle size. The purpose of continuously producing this homogeneous, moving mass of particulate material is to permit the application of one or more coating media, which previously have been reduced to liquid state by melting, dissolution in a solvent, or other means, by spraying the atomized liquid coating media from a multitude of conventional liquid spray nozzles onto each moving particle uniformly with respect to the particle surface and in essentially equal amounts on each particle, thus providing a uniform coating. The novelty of the instant invention lies in the unique modification of the existing prior art of flighted, horizontal, rotary drum coolers and dryers, the rolling beds and the showering curtains of particles of which those versed in the art are thoroughly familiar. This modification also forms a larger sprayable area of the homogeneous mass of moving particles, said area consisting, in part, of the surface of the natural rolling bed of the drum as known in prior art, and in part of the face of a falling cascade of particles that extends the entire length of the drum, but, in contrast to prior art, is concentrated to one side of the drum into a dense, homogeneous, narrow stream of particles that covers only a small portion (say 1 to 10 percent) of the cross sectional area of the drum. This continuous cascade is formed by positioning by means of fixed supports extended into the end openings of the drum a stationary longitudinal deflector pan above the rolling bed in the interior of the drum. Said deflector pan extends the length of the drum and is sloped downward across its width toward the high edge of the rolling bed, the nature of which is familiar to those versed in the art of horizontal rotary drum cooler and dryer operation, so that the showers of particles being discharged by the lifting flights, as known in prior art, are caught by the deflector pan, the effective (horizontally projected) width of which may be 40 to 80 percent of the drum diameter, where they combine and slide off the lower edge of the pan to form the dense, homogeneous cascade that strikes the rolling bed near its high side and along its entire length. Variation of the effective cross sectional width of the deflector pan permits variation in the height above the bed at which the pan may be mounted and thus the height and sprayable area of the falling cascade.

The principal advantages of the instant invention over the prior art, examples of which have already been discussed, are as follows: (a) an essentially random motion of particulate solids and the resulting homogeneity of the mass with respect to particle size is achieved in a simple flighted horizontal rotary drum, thus making possible uniformity of exposure to atomized coating media not possible in unflighted (smooth) rotary drums in which segregation with respect to particle size cannot be eliminated; (b) optimization of the effect of spray distance (distance from spray nozzle to particle) is easily accomplished by moving the spray nozzles to the proper distance away from the rolling bed and from the face of the dense but relatively thin falling cascade of particles; (c) the capacity of the unit is high as compared with a fluidized bed, thus reducing cost and space; (d) the degree of superheat of a molten coating medium may be significantly reduced because of the closely controllable spray distance described above; (e) because of the nearly randomized motion of the particles with respect to each other and the ease of optimization of spray distance, the spray nozzles may be aimed at any portion of the bed or curtain without affecting the coating uniformity on individual particles, thus permitting multiple rows of spray nozzles, which in turn permits a larger number of spary nozzles per unit length of drum; this reduces the cost of the coating unit and permits better visual control of the operation; (f) the spray nozzles are not subject to bombardment by falling particles that occurs in a full cross section curtain of falling particles of prior-art methods; thus, agglomeration by molten substrate is eliminated and observation of the operation of the individual spray nozzles is possible, a simple factor which permits closer control of the proportions of substrate and coating media; (g) in granulation (increase in particulate size from undersize to product size as in fertilizer production), a true layering effect is achieved, which increases the product density, hardness, strength, and uniformity as compared with prior art, such as paddle mixer (pugmill), smooth rotary drum, and inclined pan granulators, which achieve granulation by agglomeration, or sticking together, of several smaller particles; and (h) the control of the variables in the simple rotary drum is uncomplicated and inexpensive.

BRIEF DESCRIPTION OF THE DRAWINGS

An understanding of the apparatus and objects of the present invention will be readily attained by those versed in the art from the following description, in which the scope of the unit is not intended to be restricted, reference being made to the accompanying drawings in which:

FIG. 1 is a transverse cross sectional view, of a semischematic nature, through the apparatus for carrying out the invention.

FIG. 2 is a longitudinal cross sectional view, of a semischematic nature, through the drum and its end fittings.

Referring now more specifically to the Figures, it may be seen that in the apparatus used for the practice of the present invention, there is hollow, elongated drum 1, the axis of which may be mounted horizontally or inclined slightly below the horizontal at the product discharge end to facilitate progressive movement of solid particulate feed material 2 from feed hopper 3 through the drum upon rotation of the drum at the desired speed by its drive (not shown) on its rollers (not shown) in a manner familiar to those versed in the art of horizontal rotary kilns, dryers, and coolers.

Entrance, of feed end, of drum 1 (as shown in FIG. 2) is provided with annular dam 4; the discharge end is similarly fitted with annular dam 5 so that particulate feed 2 from feed hopper 3 entering through fixed feed chute 6, which projects through the circular opening in dam 4, will be retained in drum 1 to form a rolling bed of particles of the desired depth in the manner familiar to those versed in the art of rotary coolers and dryers.

The product discharge end of drum 1 is fitted with essentially gas-tight sealed manifold assembly 7, also familiar to those versed in the art of rotary drum cooler and dryer design. In the lower side of the manifold is product discharge port 8 which collects and discharges the product spilling over dam 5. At the top of the manifold is gas port 9 through which the cooling, heating, or ventilation gases are drawn by a gas blower or other means.

Fixed at regular intervals, as shown in FIG. 1, to the internal surface, or wall, of drum 1 and rotating with it is a plurality of essentially longitudinal lifting vanes 10, or flights, that run essentially the entire length of the drum and parallel to the axis of the drum and extend from the internal surface in a generally radial direction. It does not limit the spirit of the instant invention to vary the cross sectional shape, number, or size of lifting vanes 10, their length with relation to that of drum 1, the degree of parallelism with the longitudinal axis of drum 1 or the general radial attitude. The precise dimensions involved in these factors may be easily proportioned so as to remain the same in drums of different sizes and production capacities. In an exemplary drum of pilot-plant size having a capacity of about 1000 pounds per hour, drum 1 may be 3 feet in diameter and 2 feet long, equipped with 16 lifting flights about 2 inches in width and about 2 feet long and fitted parallel to the drum axis. Feed end dam 4 and discharge end dam 5 are 4 inches high; thus the ratio of bed depth to flight width is about 2:1.

The ratio of bed depth to radial flight width may vary from about 1:1 to about 6:1 without affecting the spirit of the instant invention, but the variation does have an effect on other design or operating criteria. At a ratio of 1:1, the width of the lifting flights would be the same as the depth of the bed; therefore there would be little or no room for spraying the coating medium onto the rolling bed without coating the flights. As a result, most or all of liquid sprays 11 would necessarily be directed at the falling cascade. This would tend to defeat one objective of the invention, i.e., to increase the sprayable area per unit length of drum, but would not reduce the uniformity of the coating. If the bed depth:flight width ratio is high, say 6:1, the lifting capacity of each flight is low with respect to the total amount of particulate material in the bed; therefore, the number of flights and the rotational speed (revolutions per minute) of drum 1 would be increased to maintain an adequate density of the falling cascade. On the other hand, a light cascade could be maintained under these conditions, and most or all of the liquid coating spray could be directed at the surface of the rolling bed. This would again tend to defeat the objective of maximizing sprayable area per unit of drum length, but would not reduce the uniformity of the coating. In cross sectional shape, some of the flights are flat, some are bent along their lengths at a shallow angle, and others are bent at a deep angle. However, for simplicity, the flights may all have the same cross sectional shape.

Lifting flights 10 may be adjustable as to the angle 12 between flight and a radius of the drum 13 passing through the line of contact between the drum wall and a flight in order to optimize the flow of the falling cascade, or the flights may be fixed to the drum wall after optimization has been accomplished on another unit.

The purpose of flights 10 is to elevate successive portions of the rolling bed of particles as the drum rotates and to empty themselves, as they rotate past the effective angle of repose of the particles, onto deflector pan 14 fixed in position by means of support bars 15 above the rolling bed and not rotating with the drum. Pan 14 is slightly longer than lifting flights 10. These showers of particles from the successive flights onto pan 14 combine as they slid toward and fall off of the low side of the deflector pan 14 to form a continuous, dense cascade of falling particles that extends the length of lifting flights 10. Pan 14 is positioned inside drum 1 so that the dense cascade of particles strikes the rolling bed far enough away from the top side of the bed to shield the lifting flights from the liquid spray that may be directed toward them as they emerge from the bed during rotation. Although pan 14 is shown as a flat, inclined tray in FIG. 1, it does not depart from the spirit of the instant invention to fabricate this overhead unit as a V-bottom, elongated hopper with the outlet slot for the falling cascade located between and lower than the two outside edges. The different cross sectional shapes of lifting flights 10 mentioned previously are not essential but are helpful in causing flight discharge at different points along the deflector pan, which in turn improves the steady flow of the falling cascade.

In still another version of the design of deflector pan 14 that in no way departs from the spirit of the instant invention, two falling cascades, similar in nature to the single cascade described previously, can be formed in the same drum to further increase the sprayable area of the homogeneous mass of moving particles per unit of drum length. This is easily accomplished by fabricating the deflector pan on the shape of an inverted V, when viewed from one end as in FIG. 1, with the apex located near the center of the upper section of the drum just beneath the arc of the lifting flights. With lifting flights properly designed, in the manner known to the art of rotary drum dryer and cooler design, a sufficient amount of the particulate bed may be lifted and discharged onto the sloping surfaces on both sides of the apex, thus splitting the total flow of particulate material into two cascades, one on each side of the drum.

A multiplicity of liquid coating media spray nozzles 11 are supported in fixed or variable positions inside coating drum 1 and under deflector pan 14, the support being derived from pipe or tubing header assembly 16 entering the drum through the opening in feed end dam 4. This header, as the name implies to those versed in the art, also serves to feed the liquid coating medium to the multiplicity of nozzles 11 attached along its length, as indicated in FIG. 2; for the sake of clarity, only one header is shown. In cases where the liquid coating medium must be maintained at an elevated temperature, the header assemblies and nozzle bodies must be heated by heating jackets or tracings of the most convenient type. More than one header assembly 16 may be used in order to insert more spray nozzles per unit of drum length than the use of only one header would permit. The header assembly or assemblies may be inserted through the openings in either the feed end dam 4, the product discharge end dam 5, or in both openings.

It does not limit the spirit of the instant invention to vary the number of spray header assemblies 16 or the number of nozzles 11 attached to and fed by each assembly since the precise numbers of units would be simply proportioned to varying sizes of coating drums having different production capacities by using in the proportioning calculations the optimum or desired spray capacity of each type of nozzle being considered.

As is indicated in FIG. 1, the liquid coating media spray from nozzles 11 in a given assembly 16 are logically directed along parallel axes toward those points of the rolling bed or the falling cascade of substrate particles that causes the axes of the nozzles to be approximately perpendicular to the bed or cascade at those points. Also logically, the nozzles are directed in such a way that the atomized liquid does not impinge on the underside of fixed pan deflector 14 or on moving flights 10 entering the rolling bed.

The type and size of the liquid coating medium spray nozzles 11 do not limit the spirit of the invention, which is in effect the impingement of a finely atomized spray of a hot, concentrated solution or anhydrous melt in a fluid state uniformly on all surfaces of individual solid particles (where the liquid quickly solidifies as it is cooled below its freezing temperature or the solvent is evaporated) in a moving mass of particles that has been rendered essentially homogeneous with respect to particle size by the action of this invention. The method of formation of the finely atomized spray is not pertinent to the invention; however, the preferred method of atomization is by use of pressure-atomizing nozzles, i.e., nozzles in which the liquid is propelled by its own pressure through a small orifice at such high velocity that the stream is broken down into small droplets. Atomization with air or other suitable gases in pneumatic spray nozzles is acceptable but usually results in relatively high mist losses of the coating medium.

In the practice of the present invention, dry, solid particulate feed 2—usually recycled fines in the granulation operation and product size granules or prills in the coating operation—is accurately metered by appropriate particulate solid feed mechanism 17 from feed hopper 3 through chute 6 into the feed end opening in dam 4 of rotating drum 1; the feed is continued until the rolling bed is established between two end dams 4 and 5 and the falling cascade is established and some discharge of particles from drum 1 is occurring. The rotational speed of the drum is adjusted (or has been fixed by previous tests) so that lifting flights 10 carry a minimum amount of particles over the top edge of the deflector pan.

At this time, the liquid coating medium, which may or may not be the same material as the particulate feed, is accurately metered and introduced by any efficient liquid metering and transport system into header assembly 16. The atomized sprays of the coating medium then issue from spray nozzles 11, which have previously been directed at the face of the falling cascade, the surface of the rolling bed, or both. The droplets of the liquid coating medium solidify quickly on contact with the individual particles by virtue of the medium's physical or chemical properties (freezing of melt, evaporation of solvent, hardening of a polymer on contact with air or other accelerator, etc.). As the individual particle moves down the length of the drum under a multiplicity of sprays and is exposed to many droplets in succession, a layer of the solidified coating media gradually builds up evenly around the substrate particle, rounding it significantly in the process. Several dissimilar coatings may thus be applied in sequence in the drum, merely by feeding the different coating media to different groups of spray nozzles located in sequence along the length of the drum.

Any dust or fumes that may be formed in coating drum 1 are swept out by a current of gas, usually air, being drawn into the feed end opening in dam 4 and out through port 9 in manifold 7 by an exhaust blower, not shown, or other means. These impurities are removed from the air stream by standard antipollution devices for recovery or disposal. This flow of air also promotes the solidification of the coating medium by maintaining the bed and cascade temperature below the freezing point of the coating medium. Instead of air, hot gases, such as flue gases, may be used to promote evaporation of solvent from a solution or suspension of the coating medium.

The proportion of coating, or coatings, to particulate substrate is controlled as desired by accurate metering, in the desired ratios, of the individual feed streams. The number of spray nozzles 11 required is determined by the production capacity desired, the proportion of coating to substrate, and the maximum designed or optimum flow rate per nozzle. The optimum, of course, depends upon the nozzle size and the density and viscosity of the liquid spray medium.

As the mass of the particulate feed gradually passes through drum 1, each particle acquires a uniform coating, or shell, of the coating medium and essentially the same proportion of coating as every other particle by virtue of the homogeneity (with respect to particle size) of the bed and cascade; that is, each particle receives essentially the same exposure to the atomized coating medium. It is this homogeneity of the rolling bed and falling cascade resulting from the superior mixing action of the flighted drum and cascade that is the essence of the present invention.

Upon completion of the pass through coating drum 1, the coated product spills over discharge dam 5 into manifold product outlet 8 and on to subsequent handling (cooling, conditioning, packaging) as required.

It is not possible to define all of the drum design conditions that would be required to properly design units for all of the uses to which the apparatus might be applied. It is believed sufficient to give examples of the application of this invention to the process used for its reduction to practice, namely, the sulfur coating of urea for the production of a controlled-release nitrogen fertilizer. To those versed in the arts of coating and granulation, it will be apparent immediately that the present invention has many process applications in these areas. The application of the apparatus of the invention includes the sulfur coating of urea or other particulate fertilizer materials but is not restricted to this use.

DESCRIPTION OF THE PREFERRED EMBODIMENTS

Figure 1:
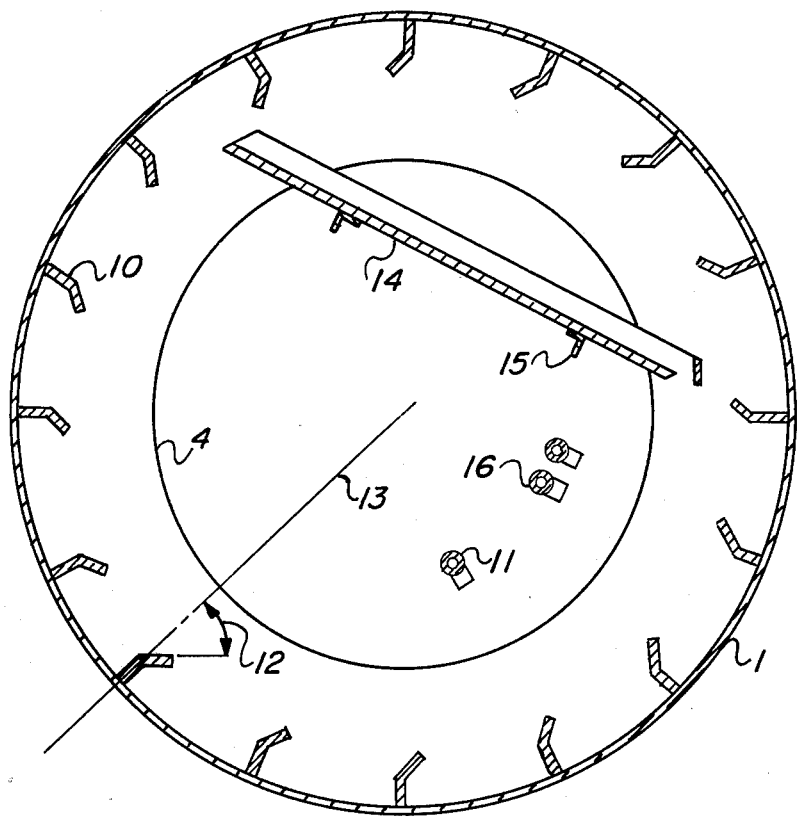
Figure 2:
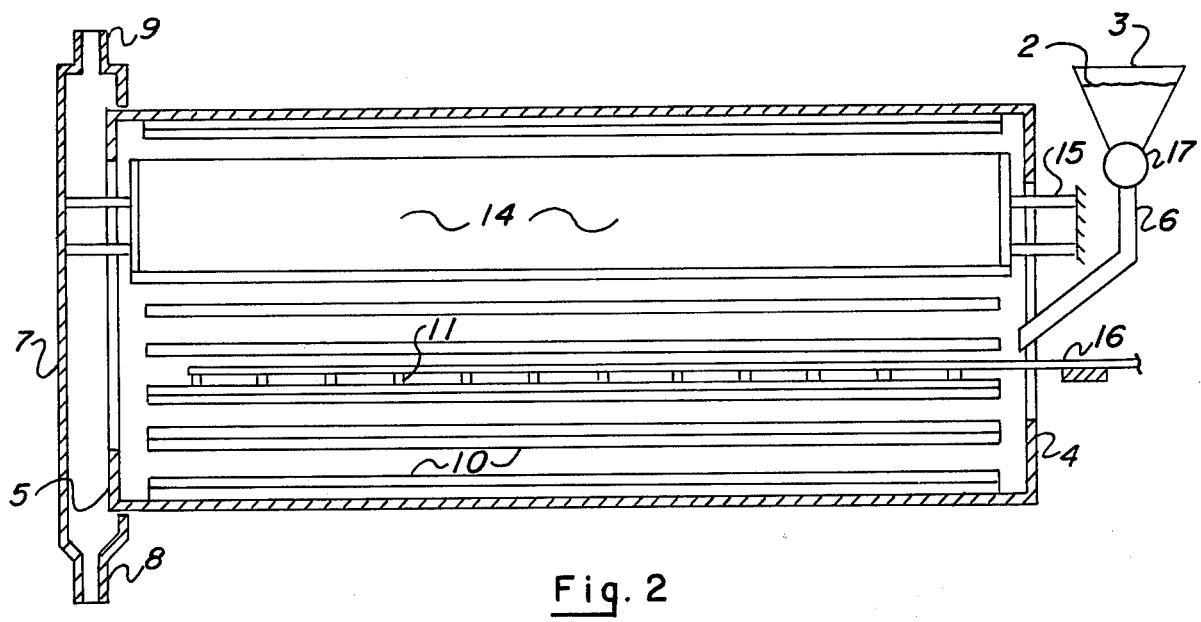

In order to demonstrate the superior results with the instant invention as compared with prior art in the formation of sulfur-coated urea, a brief description of the laboratory method of evaluating such sulfur-coated fertilizers is necessary. This method has been demonstrated to correlate with actual plant growth (agronomic) test results. The coating controlled the release of nitrogen to the growing plants, increasing the efficiency of use of the nitrogen. The laboratory method described below was used to predict relative rates of release.

A 50-gram sample of coated product is immersed in 250 milliliters of water held at 100 ±1° F in a constant-temperature oven for 7 days. At the end of that period, the urea concentration in the water is measured and the proportion (weight percent) of urea that has been dissolved from the coated granules is calculated. For a given weight percent of coating (determined by other means), the dissolution rate (weight percent dissolved in 7 days) is an inverse function of the uniformity of the coating; that is, the lower the dissolution rate for a given coating weight, the higher the degree of uniformity of the coating. For example, two sulfur-coated urea products have 25 percent coating weights; one has a 7-day dissolution rate of only 5 percent while the other has a 7-day dissolution rate of 25 percent. Obviously, the same amount of coating material has been much more uniformly applied in the low dissolution rate product than in the high because the short term dissolution rates are a direct measure of the imperfections in the coatings. Results in a small pilot plant have shown such variations to be realistic.

The following examples of the significant improvement in coating quality as applied to the production of sulfur-coated urea are the result of the installation of the apparatus of this invention in a small pilot-plant coating drum 3 feet in diameter, the sulfur-coating section of which was 2 feet long. It was mounted horizontally on rollers and equipped with a variable speed drive that drove the drum at a speed of 4 to 15 rpm. Transverse dams at either end of the coating section permitted adjustment of the bed depth from 2 inches to 4 inches.

The unit was operated first as a smooth drum (without flights and deflector pan) and then the apparatus of this invention was installed, and the unit was operated under conditions that were otherwise the same as in the smooth drum operation except as noted in the tabulations below. In all cases, a commercial granular urea (98 percent −6 +10 mesh) was used as the substrate.

Example I: Hollow-cone, pressure atomizing nozzles (0.029-inch orifices); two nozzles 10 inches apart; 700 psig sulfur pressure

| | Smooth drum | Flights and pan |
|---|---|---|
| Production rate, lb/hr | 550 | 950 |
| Drum speed, rpm | 15 | 9 |
| Bed depth, in. | 2½ | 4 |
| Spray distance, in. | 5 | 5 |
| | 7-day dissolution rate, wt. % | |
| Coating weight, wt.%[a] | Smooth drum | Flights and pan |
| 23 | 30 | 10 |
| 25 | 23 | 6 |
| 27 | 18 | 4 |

[a]Includes 3 percent microcrystalline wax and 2 percent diatomaceous earth conditioner per prior art described in U.S. patents 3,295,950 and 3,342,577 cited in this application; these additional materials added to aliquot sulfur base coated product in the laboratory under identical standard conditions.

It is important to note that the apparatus of this invention not only produced much more uniform and effective coatings for equal coating weight as evidenced by the much lower 7-day dissolution rates as compared with the smooth drum products but also increased the capacity of the unit from 550 pounds per hour to 950 pounds per hour. When the data are plotted as coating weight versus dissolution rate, they show that at a given dissolution rate of 18 percent the coating weight required on the smooth drum products is 27 percent, whereas that for the product of this invention is only 21 percent, a 22 percent reduction even without consideration of the almost twofold increase in production rate.

Example II: Hollow-cone, pressure atomizing nozzles (0.023-inch orifices); two nozzles 10 inches apart; 700 psig sulfur pressure

| | Smooth drum | Flights and pan |
|---|---|---|
| Production rate, lb/hr | 600 | 650 |
| Drum speed, rpm | 15 | 9 |
| Bed depth, in. | 2½ | 4 |
| Spray distance, in. | 5 | 5½ |
| Coating weight, wt.%[a] | 7-day dissolution rate, wt.% | |
| 23 | 23 | 7 |
| 26 | 14 | 5 |

[a]See footnote a, Example I.

The smaller pressure atomizing nozzles (0.023-in orifice) used in this test normally give results superior to those of the larger (0.029-in orifice) nozzles of the same type when used in the smooth drum (compare smooth drum, Examples I and II). However, the apparatus of this invention minimized the difference in results (compare flights and pan, Examples I and II) but still resulted in a great improvement in coating uniformity and therefore a reduction in product dissolution rates.

SUBSEQUENT WORK

As a result of the successful demonstration of the beneficial effects of the falling cascade apparatus in the small pilot plant, as conclusively demonstrated by the examples above, an entirely similar modification was installed in a larger sulfur-coated urea pilot plant that had been designed for a capacity of 2000 pounds per hour on the basis of operating data supplied from the small pilot plant described previously (without the cascade apparatus). The large unit had been operated extensively with hydraulic spray nozzles but without the cascade arrangement and the maximum rate at which satisfactory product could be produced was determined to be about 2000 pounds per hour, the designed capacity.

The large unit was modified to provide the falling cascade in a manner entirely similar to that described previously for small pilot plant, except for the dimensions and number of the lifting flights 10, the dimensions of the annular dams 4 and 5 and the deflector pan 14, and for the number of spray nozzles 11, referring to the Figures, which are entirely applicable to the larger plant. These items were sized to fit the larger coating drum 1, which is 4 feet in diameter and 6 feet in length. Specifically, the lifting flights are 24 in number, 3 inches wide, and 6 feet long. The annular dams are 5 inches high. The deflector pan is 20½ inches wide and 6 feet long and is suspended at an angle of 35° from the horizontal, as seen from the end of the drum; it is equipped with a deflector plate along the lower edge as in the small plant. Eight hydraulic spray nozzles are mounted in a single header running the length of the drum; the sprays of molten sulfur are directed at the falling cascade.

EXAMPLE III

The following is an example of the significant increase in production capacity as applied to the production of sulfur-coated urea in the large pilot plant as the result of the installation of the apparatus of this invention.

Solid-cone, oval pattern, pressure atomizing nozzles (0.011-inch orifice); 8 nozzles 8 inches apart; 780 psig to 2100 psig[a] sulfur pressure.

|  | Smooth Drum | Flights and Pan |
|---|---|---|
| Production rate, lb/hr | 2000 | 4000 |
| Drum speed, r/min | 24 | 13 |
| Bed depth, inches | 3¾ | 5 |
| Spray distance, inches | 5½ | 5½ |
| | 7-day dissolution rate, wt.% | |
| Coating weight, wt.%[b] | Smooth Drum | Flights and Pan |
| 20.5 | 20 | 14 |
| 22.4 | 15 | 8 |

[a] Pressure variation required to vary sulfur feed rate.
[b] Includes 2 percent microcrystalline wax and 2 percent diatomaceous earth conditioner per prior art described in U.S. patents 3,295,950 and 3,342,577 cited in this application, these additional materials added in waxing and conditioning sections of the large pilot plant.

As in Example I for the small pilot plant, it is important to note that the apparatus of this invention not only produced more uniform and effective coatings for equal coating weights as evidenced by the much lower 7-day dissolution rates as compared with the smooth drum products, but also increased the maximum capacity of the plant from 2000 pounds per hour to 4000 pounds per hour--a 100-percent increase.

As previously mentioned, the highly significant improvement in uniformity and quality of the coatings applied by the method and apparatus of this invention, as demonstrated conclusively in the examples above, will immediately demonstrate to those versed in the arts of coating and granulation the applicability of the apparatus of additional uses such as: (a) coating of pelletized medicinal compounds for controlled-release properties or for the purpose of making the compounds more palatable or for the purpose of adding other active ingredients; (b) coating of pelletized food products, and (c) coating of undersized fertilizer particles with the same or different fertilizer compounds for the purpose of granulation, i.e., increasing the undersize material to product size material.

The principal features of the method and apparatus of this invention are:

The flights and falling cascade provide a highly homogeneous bed and falling cascade of particles with respect to particle size.

The homogeneity of the bed and cascade permits equal exposure of all particles to the multitude of atomized liquid coating media sprays, thus ensuring uniform coatings on each particle. This permits a substantial reduction in amount of coating for certain processes such as controlled-release fertilizers or pharmaceuticals and increases drum capacity.

The falling cascade, being homogeneous with respect to particle size and by virtue of its height above the bed, increases the sprayable area of the coating drum per unit length of the drum as compared with a drum without the cascade, thus permitting the installation of a greater number of spray nozzles per unit length of drum. This shortening of the length of the drum per unit of capacity reduces its cost, gives greater visual control of the spray nozzles, and makes maintenance easier.

Varying the cross sectional shape of the deflector pan from the flat plate or hopper type to an inverted V shape permits the formation of a double cascade, one on either side of the drum; the additional cascade provides still more sprayable area per unit of drum length.

The homogeneity of the rolling bed in the flighted drum permits spraying on any portion of the bed that is free of the rotating flights and thus also yields a greater sprayable area of bed than is possible with an unflighted (smooth) drum. This permits further reduction in drum length.

The use of the flighted drum and falling cascade permits relatively fixed distances between the spray nozzles and the surfaces of the bed and cascade. This permits an easy adjustment to optimum spray distance, a factor critical to coating quality. This is not possible in prior art (full cross sectional falling curtain arrangements in rotary drums).

The easily optimized spray distance (above) permits the use of lower degrees of superheat on molten coating media because provision need not be made to prevent some of the freezing prior to impingement on the substrate that occurs in prior art (full curtain drum).

The deflector pan prevents contact between the nozzles and the moving mass of particles in the bed and cascade, thus preventing agglomeration of some of the substrate by the molten substrate dripping from the hot nozzles that occurs with prior art (full cross sectional falling curtain arrangements in rotary drums).

The present invention is simply, easily, and very economically applied to rotary drum operation which is widely used in particulate solid processing and which inherently permits high tonnage production capacity per unit cost.

The uniform coating effect achieved in this invention, when applied to a granulation process, yields a rounded, dense, strong granule superior to those produced in prior art (rotary drum, pan, and paddle mixer granulation).

The variables involved in rotary drum operation (coolers, dryers, kilns, etc.) are inherently easy to control, so sophisticated instrumentation and close operator control are not required.

While I have shown and described particular embodiments of my invention, modifications and variations thereof will occur to those skilled in the art. I wish it to be understood, therefore, that the appended claims are intended to cover such modifications and variations which are within the true scope and spirit of my invention.

What I claim as new and desire to secure by Letters Patent of the United States is:

1. A process for the formation of coated rounded particles of substantially uniform size which comprises introducing the material to be coated into the inlet end of a rotating drum, the axis of which drum is maintained in a generally horizontal attitude; therein maintaining a bed of rolling discrete nuclei particles of substance to be coated in which bed said nuclei are in contact with each other, said rotating drum having lifting flights on the inner surface thereof acting to elevate portions of said bed from the bottom of said drum to a higher point therein; releasing said elevated portions of said bed on said lifting flights and cascading same onto a generally horizontally inclined plane over substantially the full upper surface thereof, said plane fixed in space inside the upper hemispherical section of said drum and extending substantially therethroughout whereby said particles are moved downwardly over the upper surface of said horizontally inclined plane to a lower edge thereof juxtaposed a sidewall of said drum, wherefrom said particles free-fall back to the bed of nuclei juxtaposed the bottom of said rotating drum; spraying localized portions of said particles after their release from the bottom edge of said inclined plane with the coating material, thereby ensuring that at least a portion of the coating material so sprayed is directed upon a dense cascade of particles which are substantially particle size homogeneous; and removing at least a portion of the resulting spray-coated particles from the outlet end of said drum; said process characterized by the fact that it ensures that the localized portion of particles, which is sprayed to effect coating thereby, is substantially particle size homogeneous, thereby effecting substantially uniform coatings on each particle released from said lifting flights.

2. A process for the formation of coated rounded particles of substantially uniform size which comprises introducing the material to be coated into the inlet end of a rotating drum, the axis of which drum is maintained in a generally horizontal attitude; therein maintaining a bed of rolling discrete nuclei particles of substance to be coated in which bed said nuclei are in contact with each other, said rotating drum having lifting flights on the inner surface thereof acting to elevate portions of said bed from the bottom of said drum to a higher point therein; releasing said elevated portions of said bed on said lifting flights, and cascading same onto substantially the full upper surface of deflector means, said deflector means fixed in space in the upper hemispherical section of said drum and extending substantially therethroughout comprising two generally horizontally inclined planes defining a generally inverted V configuration, moving said particles away from the apex of said inverted V and toward each of the two bottom edges thereof, each said edge juxtaposed a sidewall of said drum wherefrom said particles free-fall back to the bed of nuclei juxtaposed the bottom of said chamber; and spraying localized portions of said particles after their release from the bottom edges of said inclined planes, thereby ensuring that at least a portion of the coating material so sprayed is directed upon a dense cascade of particles which are substantially particle size homogeneous; and removing at least a portion of the resulting spray-coated particles from the outlet end of said drum; said process characterized by the fact that it ensures that the localized portion of particles, which is sprayed to effect coating thereby, is substantially particle size homogeneous, thereby effecting substantially uniform coatings on each particle released from said lifting flights.

* * * * *